United States Patent [19]
Kjell et al.

[11] Patent Number: 5,750,688
[45] Date of Patent: May 12, 1998

[54] PROCESS FOR PREPARING BENZOIC ACID DERIVATIVE INTERMEDIATES AND BENZOTHIOPHENE PHARMACEUTICAL AGENTS

[75] Inventors: Douglas P. Kjell; Fred M. Perry, both of West Lafayette, Ind.

[73] Assignee: Eli Lilly and Company, Indianapolis, Ind.

[21] Appl. No.: 629,862

[22] Filed: Apr. 9, 1996

Related U.S. Application Data

[62] Division of Ser. No. 298,636, Aug. 31, 1994, Pat. No. 5,631,369.

[51] Int. Cl.[6] .................... C07D 407/12; C07D 333/72
[52] U.S. Cl. .................... 540/596; 544/146; 546/213; 548/525; 549/55
[58] Field of Search ................ 544/146; 546/213; 548/525; 540/596; 549/55

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |
| 4,656,187 | 4/1987 | Black et al. | 514/422 |

OTHER PUBLICATIONS

Pinney et al., Journal of Organic Chemistry, 56(9), 3125–3133, 1991.
Pinney et al., Steroids, 57(5), 222–232, 1992.
Jones et al, Journal of Medicinal Chemistry, 22(8), 1057–1066, 1984.
Jones, C.D., et al. *J. Med. Chem.*, 27:1057–1066 (1984).

*Primary Examiner*—Matthew V. Grumbling
*Attorney, Agent, or Firm*—Janelle D. Strode; David E. Boone

[57] ABSTRACT

Novel processes are provided for producing compounds of formula II

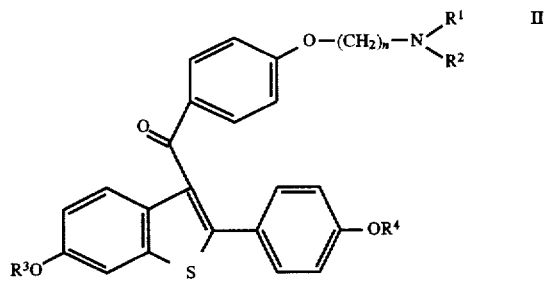

wherein
$R^1$ and $R^2$ each are independently $C_1$–$C_4$ alkyl, or combine to form piperidinyl, pyrrolidinyl, methylpyrrolidinyl, dimethylpyrrolidinyl, morpholino, dimethylamino, diethylamino, or 1-hexamethyleneimino;
$R^3$ and $R^4$ each are H or a hydroxy protecting group; and
n is 2 or 3;
or a pharmaceutically acceptable salt thereof by reacting a haloalkylamine with a phenolic ester in the presence of an alkylacetate solvent and a base.

15 Claims, No Drawings

PROCESS FOR PREPARING BENZOIC ACID DERIVATIVE INTERMEDIATES AND BENZOTHIOPHENE PHARMACEUTICAL AGENTS

This application is a division of application Ser. No. 08/298,636 filed Aug. 31, 1994 now U.S. Pat. No. 5,631,369, issued May 20, 1997.

FIELD OF THE INVENTION

The present invention relates to the fields of pharmaceutical and organic chemistry and provides novel processes for preparing compounds of formula I

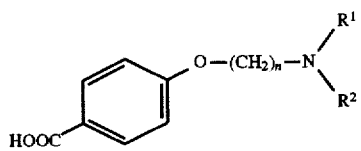

wherein $R^1$ and $R^2$ each are independently $C_1$–$C_4$ alkyl, or combine to form piperidinyl, pyrrolidinyl, methylpyrrolidinyl, dimethylpyrrolidinyl, morpholino, dimethylamino, diethylamino, or 1-hexamethyleneimino; and n is 2 or 3;

or a pharmaceutically acceptable salt thereof, compound of formula II

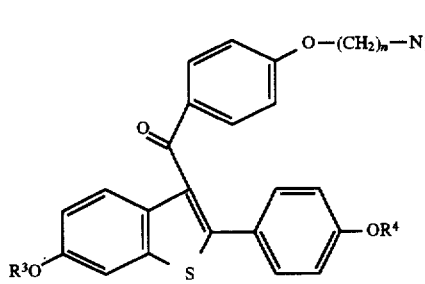

wherein $R^3$ and $R^4$ each are H or a hydroxy protecting group; and $R^1$, $R^2$ and n are as defined above; or a pharmaceutically acceptable salt thereof.

Compounds of formula II, particularly raloxifene, in which $R^1$ and $R^2$ combine to form a piperidinyl moiety, $R^3$ and $R^4$ each are H, and n is 2, are well known in the pharmaceutical art as having activity for the treatment of certain disease states including, for example, osteoporosis.

BACKGROUND OF THE INVENTION

Typically, compounds of formula I are prepared by reacting, for example, β-chloroethylpiperidine hydrochloride and ethyl 4-hydroxybenzoate in methyl ethyl ketone, in the presence of potassium carbonate (see, U.S. Pat. No. 4,418,068.) However, the referenced synthetic route has certain undesirable aspects. Firstly, the solvent, methyl ethyl ketone, is hazardous and requires expensive handling and disposal procedures. Secondly, use Of this solvent sets a limit of 80° C. as a reaction temperature during formation of an ester, thus limiting the rate of the potassium carbonate catalyzed alkylation reaction. Furthermore, the organic layer containing the ester must be stripped to an oil prior to dissolution of the oil in aqueous sodium hydroxide and methanol. This oil preparation step is time consuming and could reduce the ultimate yield with large-scale production.

Thus, a more efficient, less expensive process for preparing compounds of formula I, and, ultimately, compounds of formula II, especially if such an efficient process did not require the use of hazardous solvents, would be a significant and desirable advance over the current state of the art. The present invention provides such a process.

SUMMARY OF THE INVENTION

The present invention provides a novel process for preparing compounds of formula I

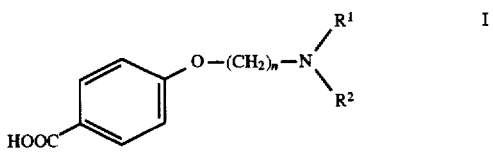

wherein $R^1$ and $R^2$ each are independently $C_1$–$C_4$ alkyl, or combine to form piperidinyl, pyrrolidinyl, methylpyrrolidinyl, dimethylpyrrolidinyl, morpholino, dimethylamino, diethylamino, or 1-hexamethyleneimino; and n is 2 or 3;

or a pharmaceutically acceptable salt thereof, comprising a) reacting a haloalkyl amine of formula III

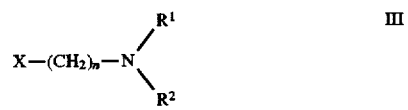

wherein

X is a halogen; and $R^1$, $R^2$, and n are as defined above, with a compound of formula IV

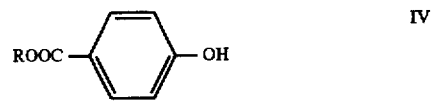

wherein R is $C_1$–$C_6$ alkyl, in the presence of an alkyl acetate solvent and a base;

b) extracting the reaction product of step a) with an aqueous acid; and c) cleaving the ester of the reaction product from step b) to form an acid.

The present invention further provides a process for preparing compounds of formula II

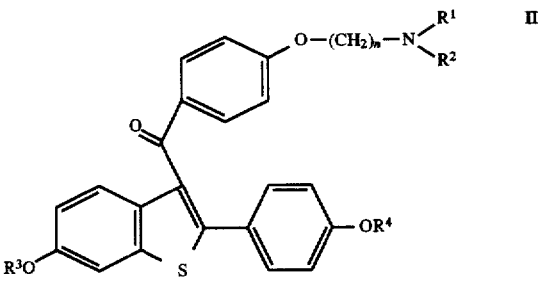

wherein $R^1$ and $R^2$ each are independently $C_1$–$C_4$ alkyl, or combine to form piperidinyl, pyrrolidino, methylpyrrolidino, dimethylpyrrolidinyl, morpholino, dimethylamino, diethylamino, or 1-hexamethyleneimino;

$R^3$ and $R^4$ each are H or a hydroxy protecting group; and n is 2 or 3;

or a pharmaceutically acceptable salt thereof, comprising a) reacting a haloalkyl amine of formula III

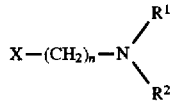

wherein

X is a halogen; and $R^1$, $R^2$, and n are as defined above, with a compound of formula IV

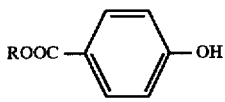

wherein R is $C_1$–$C_6$ alkyl, in the presence of an alkyl acetate solvent and a base;

b) extracting the reaction product from step a) with an aqueous acid;

c) cleaving the ester of the reaction product from step b) to form an acid;

d) reacting the extracted product from step c) with a compound of formula V

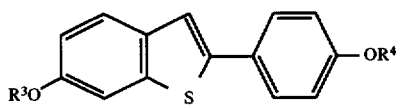

wherein $R^3$ and $R^4$ are as defined above, or a pharmaceutically acceptable salt thereof;

e) optionally removing the $R^3$ and $R^4$ hydroxy protecting groups of the reaction product from step d); and f) optionally forming a salt of the reaction product from either steps d) or step e).

DETAILED DESCRIPTION OF THE INVENTION

One aspect of the present invention provides a process for preparing a compound of formula I

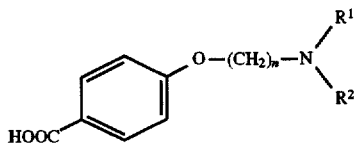

wherein $R^1$ and $R^2$ each are independently $C_1$–$C_4$ alkyl, or combine to form piperidinyl, pyrrolidinyl, methylpyrrolidinyl, dimethylpyrrolidinyl, morpholino, dimethylamino, diethylamino, or 1-hexamethyleneimino; and n is 2 or 3;

or a pharmaceutically acceptable salt thereof, comprising a) reacting a haloalkyl amine of formula III

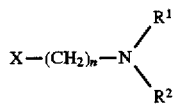

wherein x is a halogen; and $R^1$, $R^2$, and n are as defined above, with a compound of formula IV

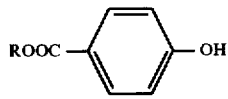

wherein R is $C_1$–$C_6$ alkyl, in the presence of an alkyl acetate solvent and a base;

b) extracting the reaction product of step a) with an aqueous acid; and c) cleaving the ester of the reaction product from step b) to form an acid.

General terms used in description of chemical formulae herein bear their usual meanings. For example, the term "$C_1$–$C_4$ alkyl" refers to straight or branched chains of 1 to 4 carbon atoms including, methyl, ethyl, propyl, isopropyl, butyl, n-butyl, and isobutyl; and the term "$C_1$–$C_6$ alkyl" encompasses the groups included in the definition of "$C_1$–$C_4$ alkyl" in addition to groups such as pentyl, isopentyl, hexyl, isohexyl, and the like.

The term "halo" includes bromo, chloro, fluoro, and iodo.

In formula II compounds, the $R^3$ and $R^4$ hydroxy protecting groups, when $R^3$ and $R^4$ are not H, denote groups which generally are not found in final, therapeutically active compounds, but which are intentionally introduced during a portion of the synthetic process to protect a group which otherwise might react in the course of chemical manipulations, and is then removed at a later stage of the synthesis. Since compounds bearing such protecting groups are of importance primarily as chemical intermediates (although some derivatives also exhibit biological activity), their precise structure is not critical. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley (New York, 1981); and *The Peptides*, Vol. I, Schrooder and Lubke, Academic Press (London and New York, 1965).

Representative hydroxy protecting groups include, for example —$C_1$–$C_4$ alkyl, —CO—($C_1$–$C_6$ alkyl), —$SO_2$—($C_4$–$C_6$ alkyl), and —CO—Ar in which Ar is optionally substituted phenyl. The term "substituted phenyl" refers to a phenyl group having one or more substituents selected from the group consisting of $C_1$–$C_4$ alkyl, $C_1$–$C_5$ alkoxy, hydroxy, nitro, chloro, fluoro, and tri(chloro or fluoro) methyl. The term "$C_1$–$C_5$ alkoxy" represents a $C_1$–$C_5$ alkyl group attached through an oxygen bridge such as, for example, methoxy, ethoxy, n-propoxy, isopropoxy, and the like. Preferred $R^3$ and R4 hydroxy protecting groups are $C_1$–$C_4$ alkyl, particularly methyl.

In the present, novel process, an equivalent amount of a haloalkyl amine of formula III is reacted with an equivalent amount of a 4-hydroxybenzoate of formula IV in the presence of an appropriate acetate solvent. A preferred formula III compound is that in which $R^1$ and $R^2$ combine to form piperidinyl, n is 2, and X is chloro, while a preferred formula IV compound is that in which R is ethyl.

Appropriate acetate solvents include those in which the alkyl moiety of such solvent is a straight or branched chain alkyl moiety having one to nine carbon atoms. The preferred solvent is amyl acetate because it is environmentally friendly, is inexpensive, and has a high boiling point which allows the alkylation to take place at relatively high temperatures. other appropriate acetate solvents include, for example, ethyl acetate, propyl acetate, isopropyl acetate, butyl acetate, isoamyl acetate, and the like.

The acetate solvents used in the present process have distinct advantages over the prior art ketone solvents such as methyl ethyl ketone. Acetate solvents are much safer than ketone solvents and require less expensive handling and disposal procedures. Equally important, acetate solvents allow the present process to be run at a higher temperature than the temperature which may be used with ketone solvents. Thus, the reaction can be run at a faster, more economical rate, and the reaction can be more complete, particularly when used for large scale production.

Furthermore, the present process obviates the need for stripping the organic layer containing a formula I compound to an oil prior to cleaving the terminal ester for reaction in the below-described process.

In addition to an alkyl acetate solvent, the present process, as well as the process described below, is run in the presence of an appropriate base. Appropriate bases include organic and inorganic bases, but inorganic bases, particularly a carbonate or bicarbonate base, is preferred. Of these, powdered potassium carbonate is especially preferred. Although the presence of a base is necessary for the present process to run, powdered potassium carbonate is the most efficient for enhancing the speed of the reaction.

Furthermore, it is preferred to maintain the alkylation reaction mixture under an inert atmosphere, such as, for example, argon, or, particularly, nitrogen.

The present reaction may be run at a temperature from about 80° C. to the reflux temperature of the solvent. A preferred temperature range is from about 100° C. to about 150° C., while a range from about 115° C. to about 120° C. is especially preferred.

The length of time for this reaction is that amount necessary for the reaction to occur. Typically, this reaction takes from about 2 to about 24 hours. The optimal time can be determined by monitoring the progress of the reaction via conventional chromatographic techniques.

Upon completion of this reaction, the alkylation mixture typically is cooled, to about 30° C. to about 70° C., and washed with water to dissolve the added basic salt. An appropriate aqueous acid is then added to the mixture to extract a compound of formula Ia

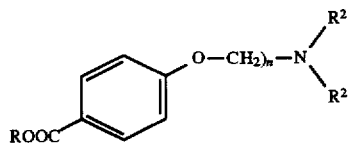

wherein

R is $C_1-C_6$ alkyl; and $R^1$, $R^2$, and n are as defined above, or a pharmaceutically acceptable salt thereof.

Preferably, aqueous hydrochloric acid is used for the extraction process, forming a hydrochloride salt of the formula I compound. Other aqueous acids such as, for example, sulfuric acid, phosphoric acid, acetic acid and the like, may be used, and the corresponding formula I acid salt is provided.

The alkyl ester of the desired formula Ia compound is then cleaved via standard procedures, providing a compound of formula I. Typically, the formula I acid extract is heated to a temperature in the range from about 80° C. to about 150° C., preferably from about 95° C. to about 100° C. At the preferred temperature range, an acceptable level of formula I compound is produced in about 4 hours. Continued heating for up to 24 hours will not affect either quality or yield. Optionally, while applying heat in the above-stated temperature range, the ester cleaving may be accelerated by distilling and removing the alcohol formed via acid hydrolysis.

Isolation and purification of the formula I acid is accomplished using procedures well known to one of ordinary skill in the art. Generally, the resulting mixture from the ester cleavage step is cooled to a temperature range from about $-5°$ C. to about 20° C. Although the product will crystallize or precipitate out of solution at this range, the optimum temperature range is from about 0° C. to about 5° C. The desired formula I compound is then isolated by filtration.

Another aspect of the invention provides a process for preparing a compound of formula II

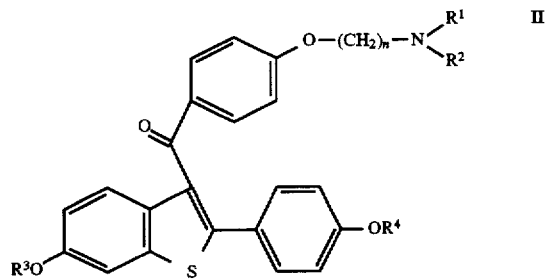

wherein $R^1$ and $R^2$ each are independently $C_1-C_4$ alkyl, or combine to form piperidinyl, pyrrolidino, methylpyrrolidino, dimethylpyrrolidinyl, morpholino, dimethylamino, diethylamino, or 1-hexamethyleneimino;

$R^3$ and $R^4$ each are H or a hydroxy protecting group; and n is 2 or 3;

or a pharmaceutically acceptable salt thereof, comprising a) reacting a haloalkyl amine of formula III

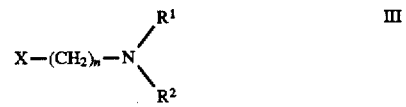

wherein

X is a halogen; and $R^1$, $R^2$, and n are as defined above, with a compound of formula IV

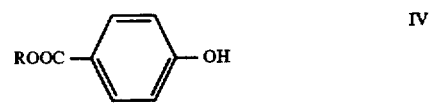

wherein R is $C_1-C_6$ alkyl, in the presence of an alkyl acetate solvent and a base;

b) extracting the reaction product from step a) with an aqueous acid;

c) cleaving the ester of the reaction product from step b) to form an acid;

d) reacting the extracted product from step c) with a compound of formula V

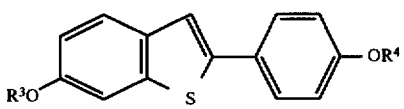

wherein $R^3$ and $R^4$ are as defined above, or a pharmaceutically acceptable salt thereof;

e) optionally removing the $R^3$ and $R^4$ hydroxy protecting groups of the reaction product from step d); and f) optionally forming a salt of the reaction product from either steps d) or step e).

For the present, novel process, steps a), b), and c) are the same as steps a), b), and c) in the above described process, plus additional step d) (acylation of a formula V compound with a formula I compound), step e) (optional removal of any hydroxy protecting group), and step f) (optional salt formation of a protected or deprotected compound of formula II).

In step d), the reaction product from step c) which, preferably, is isolated and purified prior to the initiation of this step, is reacted with a compound of formula V

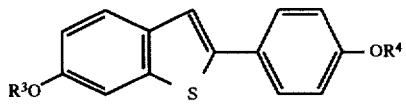

wherein $R^3$ and $R^4$ are as defined above.

Compounds of formula V, are known in the art and are prepared, for example, as described by Peters in U.S. Pat. No. 4,380,635, or Jones, et al., in U.S. Pat. Nos. 4,133,814 and 4,418,068, each of which is herein incorporated by reference. Although the $R^3$ and $R^4$ protecting groups are not required for this step, thus allowing a compound of formula V in which $R^3$ and $R^4$ are hydrogen to be acylated with a compound of formula I in which $R^3$ and $R^4$ each are hydrogen, one skilled in the art would recognize that a hydroxy protecting group, particularly methyl, would be preferred. A preferred formula I compound for the present acylation reaction is that in which $R^1$ and $R^2$ are combined for form piperidinyl and n is 2.

Reagents and all parameters necessary to carry out the acylation step of step d), the optional deprotection step of step e), the optional salt formation step of step f), and isolation and purification of formula II compounds are described in the afore-incorporated United States patents. Thus, pharmaceutically active compounds of formula V, including their acid addition salts, are prepared via the instant process of the present invention.

The following examples are provided for the purpose of illustrating the present invention and are not intended to be limiting upon the scope of the invention.

EXAMPLE 1

Preparation of 4-(2-piperidinoethoxy)benzoic acid hydrochloride: prior art method To a 250 mL 3 neck flask equipped with mechanical stirring, condenser, and a resistance thermal device (RTD probe) connected via temperature controller to a heating mantle and under nitrogen atmosphere were added: 8.31 g of ethyl 4-hydroxybenzoate, 11.05 g of β-chloroethylpiperidine hydrochloride, 16.59 g of potassium carbonate, and 60 mL methyl ethyl ketone. The mixture was heated to 80° C. for 4 hours. Thin layer chromatography (TLC), conducted in solvent system comprising 20 parts ethylene acetate and 5 parts isopropyl alcohol, showed the reaction to be complete. 60 mL water was added at ambient temperature and the mixture was stirred for 30 minutes. The aqueous layer was separated and discarded. The organic layer was concentrated at 40° C. with an aspirator vacuum to an oil to yield 15.65 g of solvent product mixture (14.4 g of product is 100% of the theoretical yield). NMR showed the reaction to be clean but contaminated with traces of water and methyl ethyl ketone. 30 mL of methanol and 15 mL of 5N NaOH were added and the solution was allowed to react at 40° C. for 4.5 hours. An aliquot was removed and shown to be extremely clean and virtually quantitative through NMR.

40 mL of water was added to the mixture, which was then cooled to 0° C.–5° C. The material was then transferred to an Erlenmeyer flask with magnetic stirring. Concentrated hydrochloric acid (18 mL) was then added and the mixture allowed to react for 1 hour. Crystallization stopped the stirrer. The crystallized 4-(2-piperidinoethoxy)benzoic acid hydrochloride was filtered and dried. Yield=13.91 g (97% theoretical).

EXAMPLE 2

Preparation of 4-(2-pireridinoethoxy)benzoic acid hydrochloride a. To a 250 mL 3 neck flask, with mechanical stirring, condenser, and RTD probe were added the following under nitrogen atmosphere: 0.05 mol methyl 4-hydroxybenzoate, 0.06 mol β-chloroethylpiperidine hydrochloride, 16.59 grams of potassium carbonate, and 60 mL of isopropyl acetate. The mixture was heated at 75° C.–80° C. for 20 hours, at which time all the methyl 4-hydroxybenzoate was consumed. 60 mL of water was then added to dissolve the potassium carbonate. The organic and aqueous phases were then separated and the aqueous layer discarded. The organic layer was washed with a second 60 mL aliquot of water; the layers were separated and the aqueous layer discarded. The reaction product, 4-(2-piperidinoethoxy)benzoic acid, methyl ester, was then extracted into 25 mL 8N hydrochloric acid. The aqueous phase was separated and the organic phase discarded. The aqueous phase was refluxed in a 50 mL round bottomed flask with magnetic stirring and condenser for 48 hours. The mixture was then cooled to 0° C.–50° C. and the crystals removed by filtration. The crystals were rinsed with acetone and dried overnight in 50° C. vacuum oven. 13.63 g of 4-(2-piperidinoethoxy)benzoic acid hydrochloride were recovered, which is 95.3% of the theoretical yield.

b. HPLC analysis indicated substantially pure 4-(2-piperidinoethoxy)benzoic acid, hydrochloride with only minor amounts of the methyl ester. The HPLC analysis was conducted as follows: A Zorbax $C_8$ column was used (length: 25 cm; diameter: 4.6 mm; particle size: 5 microns). A weak eluent (60 mM phosphate and 10 mM octane sulfonate) was prepared by combining 6.48 g sodium 1-octanesulfonate and 12 mL HPLC grade concentrated phosphoric acid. This mixture was diluted to 3 L with HPLC, water and the resulting solution was adjusted to pH 2 with sodium hydroxide. Acetonitrile was employed as a strong eluent. A solution of 60% weak eluent, 40% strong eluent was applied to the column at a flow rate of 1 mL/minute; detection -247 nm. Under the foregoing conditions, elution of the methyl ester occurred in five minutes; the unreacted acid eluted in 3.5 minutes.

EXAMPLE 3

Preparation of 4-(2-piperidinoethoxy)benzoic acid hydrochloride with methyl 4-hydroxybenzoate and β-chloroethylpiperidine hydrochloride To a 125 mL 3 neck flask with mechanical stirring, condenser, and RTD probe under nitrogen atmosphere the following were added: 7.61 g methyl 4-hydroxybenzoate, 11.05 g β-chloroethylpiperidine hydrochloride, 16.59 g powdered potassium carbonate and 60 mL isopropyl acetate. The mixture was plunged into an oil bath and the reaction reached 52° C. The bath temperature was gradually raised over approximately one hour until the reaction reached 75° C.–80° C. HPLC results over time:

| Time | Methyl 4-hydroxybenzoate | Methyl 4-(2-piperidinoethoxy) benzoate |
|---|---|---|
| $T_o$ (at 75° C.–80° C.) | 88% | 12% |
| 0.75 hour | 72% | 28% |
| 2.33 hours | 46% | 54% |
| 6 hours | 14% | 86% |
| >18 hours | 0% | 100% |

The mixture was cooled to ambient temperature and 60 mL water was added to dissolve solids. The aqueous layer was separated and discarded. The organic layer was washed with 60 mL water. The ester product was extracted into 25 mL 8N hydrochloric acid. The HCl extract was heated to 95° C. in original apparatus overnight and then cooled to 0° C.–50° C. for 1 hour. The resulting crystals were filtered, rinsed with acetone and dried. Yield: 12.92 g (91.3% theoretical).

EXAMPLE 4

Preparation of 4-(2-piperidinoethoxy)benzoic acid hydrochloride

To a 250 mL 3 neck flask equipped with mechanical stirring, condenser, and heating apparatus consisting of a RTD probe hooked via a temperature controller to a heating mantle and under nitrogen atmosphere, the following were added: 7.61 g methyl 4-hydroxybenzoate, 11.05 g β-chloroethylpiperidine hydrochloride, 16.59 g powdered potassium carbonate, and 60 ML isopropyl acetate. The mixture was heated slowly to 80° C. After 5 hours, high performance liquid chromatography showed reaction to be 90% complete. After being left overnight at 80° C., reaction was complete. The mixture was then cooled to ambient temperature, after which 60 mL deionized water was added. The mixture was stirred until all solids dissolved. The aqueous layer was separated and discarded.

The organic layer was extracted 3 times with 20 mL 4N hydrochloride. The combined aliquots, containing 4-(2-piperidinoethoxy)benzoic acid, ethyl ester, were heated at reflux (92° C., 30 minutes required to reach reflux). After 7.5 hours at reflux, the mixture was then distilled to remove approximately 10 mL water and cooled in an ice bath for 15 minutes. The resulting crystalline 4-(2-piperidinoethoxy) benzoic acid, hydrochloride was removed by filtration and rinsed with acetone and dried. Yield=12.53 g of product (87.7% of theoretical).

EXAMPLE 5

Preparation of 4-(2-piperidinoethoxy)benzoic acid hydrochloride

To a 125 mL 3 neck flask with mechanical stirring, condenser, and a heating apparatus consisting of an RTD probe hooked via a temperature controller to a heating mantle, the following were added: 7.61 g methyl 4-hydroxybenzoate, 11.05 g β-chloroethylpiperidine hydrochloride, 16.59 g powdered potassium carbonate, and 60 mL amyl acetate. The mixture was heated in an oil bath under nitrogen to 115° C.–120° C. for 4 hour. HPLC indicated that the reaction was complete. The mixture was then cooled to ambient temperature and 40 mL of deionized water were added to dissolve solids. The aqueous layer was separated and discarded and the water wash was repeated. 5 mL of the organic phase was removed as an analytical standard. 25 mL 8N hydrochloric acid was added to remaining organic phase to extract the intermediate. The layers were separated and the acidified aqueous layers returned to the reaction flasks. The organic phase was discarded. The aqueous phase was heated to 95° C. until HPLC indicated complete hydrolysis of the ester (about 4 hours). The mixtures were cooled to 0° C.–5° C. for 1 hour and filtered. The filter cakes were rinsed with acetone (approx. 25 mL) and dried. Yield -12.61 g (83.6% theoretical).

EXAMPLE 6

Preparation of 4-(2-piperidinoethoxy)benzoic acid hydrochloride

To a 125 mL 3 neck flask with mechanical stirring, condensers, and a heating apparatus consisting of an RTD probe in the flask hooked via a temperature controller to a heating mantle, the following were added: 7.61 g methyl 4-hydroxybenzoate, 11.05 g -chloroethylpiperidine hydrochloride, 16.59 g powdered potassium carbonate, and 60 mL amyl acetate. The mixture was slowly heated under nitrogen in an oil bath to 97° C. The reaction was allowed to proceed overnight. The mixture was cooled to ambient temperature and 40 mL deionized water was added to dissolve the solids. The aqueous layer was separated and discarded and the water wash repeated. 25 mL of 8N hydrochloric acid were added in a single aliquot to extract the intermediate. The layers were separated and the acidic aqueous layer returned to the reaction flask. The aqueous layer was heated to 95° C. and the reaction was allowed to proceed for 24 hours as a stress test. After 6 hours, 0.3% of ester remained. The mixture was cooled to 40° C. and 25 mL acetone was added. The mixture was cooled to 0° C.–5° C. for 1 hour. The filter cakes were rinsed with approx. 25 mL acetone and dried. HPLC revealed 0.2 g of product in filtrate. Yield (crystalline) 13.38 g (95.1% of theoretical).

EXAMPLE 7

Preparation of 4-(2-piperidinoethoxy)benzoic acid hydrochloride

To a 125 mL 3 neck flask with mechanical stirring, condenser, and a heating apparatus consisting of an RTD probe in the flask hooked via a temperature controller to a heating mantle, the following were added: 7.61 g methyl 4-hydroxybenzoate, 11.05 g β-chloroethylpiperidine hydrochloride, 16.59 g powdered potassium carbonate, and 60 mL amyl acetate. The mixture was heated overnight under nitrogen in an oil bath to 125° C., and was allowed to proceed until HPLC indicated complete consumption of the methyl 4-hydroxybenzoate. The mixture was cooled to ambient temperature and 40 mL deionized water was added to dissolve the solids. The aqueous layer was separated and discarded. The water wash was repeated. 25 mL of 8N hydrochloric acid were added to extract intermediate. The layers were separated and the acid layer returned to the reaction flask. The acid solution was heated to 95° C. for about 24 hours as a "stress" test; (after 6 hours 1% of the uncleaved ester remained.) The mixture was cooled to 40° C. and 25 mL acetone added. The mixture was cooled to 0°

EXAMPLE 8

Preparation of 4-(2-piperidinoethoxy)benzoic acid hydrochloride

To a 100 mL round bottom flask equipped with mechanical stirring and condenser, and a heating apparatus consisting of an RTD probe in the flask hooked via a temperature controller to a heating mantle, the following were added: 4.155 g ethyl 4-hydroxybenzoate, 5.985 g β-chloroethylpiperidene hydrochloride, 9.295 g potassium carbonate and 30 mL amyl acetate. The reaction mixture was heated to 120° C. under nitrogen and monitored by HPLC. The mixture was allowed to react at this temperature for approximately 5 hours. The reaction mixture was cooled to approximately 50° C. and 20 mL of distilled water was added to dissolve the solids. The mixture was cooled to ambient temperature. The aqueous layer was separated and discarded. The water wash was then repeated. 12.5 mL of 8N hydrochloric acid were added with stirring to extract the analysis indicated complete reaction. The acid extract was heated to 95° C. until HPLC. The mixture was then cooled to less than 40° C., at which time 12.5 mL acetone was added. The mixture was then further cooled to 0° C.–5° C. and the precipitate filtered. The filter cake was rinsed with acetone and dried. Yield=5.19 g solid.

EXAMPLE 9

Preparation of 4-(2-piperidinoethoxy)benzoic acid hydrochloride

To a 250 mL 3 neck flask with mechanical stirring and condenser, and a heating apparatus consisting of an RTD probe in the flask hooked via a temperature controller to a heating mantle and under nitrogen atmosphere, the following was added: 7.61 g of methyl 4-hydroxybenzoate, 11.05 g of β-chloroethyl-piperidine hydrochloride, 16.59 g of powdered potassium carbonate and 60 mL of ethyl acetate. The mixture was heated slowly to reflux. After overnight reflux, the mixture was cooled to ambient temperature, after which 60 mL of deionized water was added. The aqueous layer was separated and discarded. The organic layer was extracted with 4N hydrochloride (3 aliquots of 20 mL). The combined acid extracts were heated to reflux. After 1 hour at reflux, HPLC indicated the saponification to be 609 complete. After 4 hours, the reaction was near 100% complete. The mixture was cooled to 0° C.–5° C. and stirred. The resulting crystals were filtered, rinsed with acetone and dried.

EXAMPLE 10

Preparation of 4-(2-piperidinoethoxy)benzoic acid hydrochloride

To two 125 mL 3 neck flasks with mechanical stirring, condensers, and a heating apparatus consisting of an RTD probe in the flask hooked via a temperature controller to a heating mantle the following were added: 7.61 g of methyl 4-hydroxybenzoate, 11.05 g of β-chloroethylpiperidine hydrochloride, 16.59 g of powdered potassium carbonate, and 60 mL of amyl acetate. The flasks were placed in an ambient oil bath and heated under nitrogen to 95° C.–100° C. The reaction was allowed to proceed until HPLC indicated 8% unreacted methyl 4-hydroxybenzoate in A, 12% unreacted in B. The flasks were then cooled to less than 50° C. 40 mL deionized water was added with stirring to dissolve solids. The aqueous layer was separated and discarded. The water wash was repeated and the aqueous layer was separated and discarded. HPLC of organic layers showed 6% 4-hydroxybenzoate remains in A, 3% in B. 25 mL of 8N hydrochloric acid was added with stirring to extract the intermediate. The layers were separated and the acid layers returned to reaction flasks. The acid solutions were heated at about 95° C. for about 4 hours. The flasks were then cooled to less than 40° C. and 25 mL of acetone was added. The mixture was then cooled to 0° C.–5° C. for 1 hour. The mixture was filtered and the cakes rinsed with approximately 25 mL of acetone and dried. A=11.50 g (80.5%), B=10.5 g (73.8%)

EXAMPLE 11

Preparation of methyl 4-(2-piperidinoethoxy) benzoic acid hydrochloride

To each of two 125 mL 3 neck flasks with mechanical stirring, condensers, and a heating apparatus consisting of an RTD probe in the flask hooked via a temperature controller to a heating mantle, the following were added: 7.61 g of methyl 4-hydroxybenzoate, 11.97 g of βchloroethylpiperidene hydrochloride, 18.59 g of powdered potassium carbonate, and 60 mL of amyl acetate. The flasks were placed in an ambient oil bath and heated under nitrogen at 120° C. for about 4 hours. The mixtures were cooled to less than 50° C., after which 40 mL of deionized water was added with stirring to dissolve solids. The mixtures were allowed to cool to ambient temperature, the layers were separated and the aqueous layer discarded. 40 mL of deionized water was added with stirring, the layers were separated and the aqueous layers discarded. 25 mL of 8N hydrochloric acid were added to each layer, with stirring, to extract the methyl esters. The layers were separated and the acid layers were returned to the reaction flasks. The mixtures were heated at about 95° C. for about 4 hours. The mixture was cooled to less than 40° C. and 25 mL of acetone was added. The mixture was cooled to 0° C.–5° C. for 1 hour. The mixture was filtered and the filter cakes rinsed with approximately 25 mL of acetone. The crystals were dried and weighed. Yield, flask A=13.10 g (92.5% of theoretical); Yield, flask B=13.05 g (90.8% of theoretical).

EXAMPLE 12

Preparation of 4-(2-piperidinoethoxy)benzoic acid hydrochloride

To a 2000 gallon tank were added: 1320 L of amyl acetate, 167.42 kg of methyl 4-hydroxybenzoate, 408.6 kg of potassium carbonate, and 283.5 kg of β-chloroethylpiperidine hydrochloride. The mixture was heated to 120° C.–125° C. for 5 hours, at which time HPLC analysis indicated complete consumption of the methyl 4-hydroxybenzoate. The tank was cooled to less than 50° C. 880 L of deionized water were added to the tank. The layers were separated and the aqueous layer was discarded. In a glass lined tank was mixed 367 L of food grade hydrochloric acid and 184 L of deionized water. The acid mixture was combined with the organic layer. The layers were separated and the organic layer was discarded. The mixture of the intermediate ester in aqueous acid heated to reflux until HPLC suggested no further consumption of the ester (13 hours). The mixture was cooled to less than 40° C. 550 L of acetone was added to the mixture and the mixture was cooled to 0° C.–5° C. and stirred for 1 hour. The product was collected by filtration on a centrifuge. The wet cake was rinsed on the centrifuge with 400 L of acetone. The product was dried in a rotary vacuum (double cone) dryer at less than 500 C and 25–27 inches in mercury. Yield was 91% of theoretical.

EXAMPLE 13

Preparation of 6-methoxy-2-(4-methoxyphenyl) benzo[b]thiophene

A 100 g portion of 3-methoxybenzenethiol and 39.1 g of potassium hydroxide dissolved in 300 mL of water were added to 750 mL of denatured ethanol, and the flask was put in a cooling bath. A total of 164 g of a-bromo-1-methoxyacetophenone was then added in small portions, and the mixture was stirred for 10 minutes in the cooling bath after the addition was complete and then for 3 hours at ambient temperature. The solvent was then evaporated off in vacuum, and 200 mL of water was added. The mixture was extracted with ethyl acetate, and the organic layer was washed twice with water, twice with aqueous sodium bicarbonate solution and twice with aqueous sodium chloride solution. The organic layer was then dried over magnesium sulfate, filtered and evaporated under vacuum to obtain 202 g of crude a-(3-methoxyphenylthio)-4-methoxyacetophenone, which was recrystallized with hexane to obtain 158 g of preferred product, m.p. 53° C.

A 124 g portion of the above intermediate was added in small portions to 930 g of polyphosphoric acid at 85° C. The temperature rose to 95° C., during the addition, and the mixture was stirred at 90° C. for 30 minutes after the addition was complete, and was then stirred an additional 45 minutes while it cooled without external heating. One liter of crushed ice was then added to the mixture, and the external ice bath was applied to control the temperature while the ice melted and diluted the acid. 500 hundred mL of additional water was added, and the light pink precipitate was filtered off and washed, first with water and then with methanol. The solids were dried under vacuum at 40° C. to obtain 119 g of crude 6-methoxy-2-(4-methoxyphenyl) benzo[b]thiophene. The crude product was slurried in hot methanol, filtered, and washed with cold methanol, and the solids were recrystallized from 4 liters of ethyl acetate, filtered, washed with hexane and dried to obtain 68 g of the desired intermediate product, m.p. 187° C.–190.5° C.

EXAMPLE 14

Preparation of Raloxifener[6-hydroxy-2-(4-hydroxyphenyl)-3- [4-(2-piperidinoethoxy)benzyl] benzo[b]thiophene hydroxchloride]

Under a nitrogen blanket, a mixture of 3 g of 4-(2-piperidinoethoxy)benzoic acid, hydrochloride, 2 drops of dimethylformamide, 2.5 mL of thionyl chloride and 40 mL of chlorobenzene was heated at 70° C.–75° C. for about 1 hour. The excess thionyl chloride and 15–20 mL solvent were then distilled off. The remaining suspension was cooled to ambient temperature and to it were added 100 mL of dichloromethane, 2.7 g of 6-methoxy-2-(4-methoxyphenyl)benzo[b]thiophene (preparation of which is described in Example 14) and 10 g of aluminum chloride. After the solution was stirred for about 1 hour, 7.5 mL of ethanethiol was added, and the mixture was stirred for an additional 45 minutes. Then 40 mL of tetrahydrofuran was added, followed by 15 mL 20% hydrochloric acid, with an exotherm to reflux. 50 mL of water and 25 mL of saturated aqueous sodium chloride were added. The mixture was stirred and allowed to cool to ambient temperature. The precipitate was collected by filtration and washed successively with 30 mL of water, 40 mL of 25% aqueous tetrahydrofuran and 35 mL of water. The solids were then dried at 40° C. under vacuum to obtain 5.05 g of product, which was identified by nuclear magnetic resonance as (6-hydroxy-2-(4-hydroxyphenyl)-3-[4-(2-pireridinoethoxy) benzyl]benzo[b]thiophene, hydrochloride).

We claim:

1. A process for preparing a compound of formula II

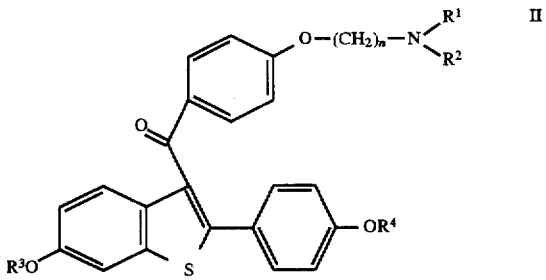

wherein $R^1$ and $R^2$ each are independently $C_1$–$C_4$ alkyl, or combine to form piperidinyl, pyrrolidinyl methylpyrrolidinyl, dimethylpyrrolidinyl, morpholino, dimethylamino, diethylamino, or 1-hexamethyleneimino;

$R^3$ and $R^4$ each are H or a hydroxy protecting group; and n is 2 or 3;

or a pharmaceutically acceptable salt thereof, comprising a) reacting a haloalkyl amine of formula III

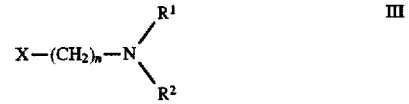

wherein
X is a halogen; and
$R^1$, $R^2$, and n are as defined above, with a compound of formula IV

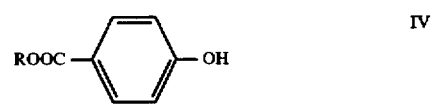

wherein R is $C_1$–$C_6$ alkyl, in the presence of an alkyl acetate solvent and a base;

b) extracting the reaction product from step a) with an aqueous acid;

c) cleaving the ester of the reaction product from step b) to form an acid;

d) reacting the extracted product from step c) with a compound of formula V

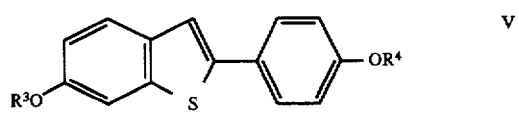

wherein $R^3$ and $R^4$ are as defined above, or a pharmaceutically acceptable salt thereof;

e) optionally removing the $R^3$ and $R^4$ hydroxy protecting groups of the reaction product form step d); and f) optionally forming a salt of the reaction product from either steps d) or step e).

2. A process according to claim 1 wherein said alkyl acetate solvent is amyl acetate.

3. A process according to claim 2 wherein said base is a carbonate or bicarbonate salt.

4. A process according to claim 3 wherein said carbonate salt is powdered potassium carbonate.

5. A process according to claim 4 wherein said formula I compound is a compound wherein $R^1$ and $R^2$ combine to form piperidinyl; and n is 2;

or a pharmaceutically acceptable salt thereof.

6. A process according to claim 4 wherein said formula II compound is a compound wherein $R^1$ and $R^2$ combine to form piperidinyl;

$R^3$ and $R^4$ each are methoxy; and n is 2;

or a pharmaceutically acceptable salt thereof.

7. A process according to claim 6 wherein said salt thereof is the hydrochloric salt.

8. A process according to claim 7 wherein said aqueous acid is hydrochloric acid.

9. A process according to claim 4 wherein said formula II compound is a compound wherein $R^1$ and $R^2$ combine to form piperidinyl.

$R^3$ and $R^4$ each are hydrogen; and n is 2;

or a pharmaceutically acceptable salt thereof.

10. A process according to claim 9 wherein said salt thereof is the hydrochloric salt.

11. A process according to claim 10 wherein said aqueous acid is hydrochloric acid.

12. A process according to claim 1 wherein said alkyl acetate solvent is isopropyl acetate.

13. A process according to claim 12 wherein said aqueous acid is hydrochloric acid.

14. A process according to claim 1 wherein alkyl acetate solvent is ethyl acetate.

15. A process according to claim 14 wherein said aqueous acid is hydrochloric acid.

* * * * *

UNITED STATES PATENT AND TRADEMARK OFFICE
CERTIFICATE OF CORRECTION

PATENT NO. : 5,750,688
DATED : May 12, 1998
INVENTOR(S) : Kjell, et al.

It is certified that error appears in the above-identified patent and that said Letters Patent is hereby corrected as shown below:

Column 8, line 21, delete "(2-pireridinoethoxy)" and insert -- (2-piperidinoethoxy) --.

Column 12, line 26, delete "βchloroethylpiperidene" and insert -- β-chloroethylpiperidene --.

Signed and Sealed this

Nineteenth Day of January, 1999

Attest:

Attesting Officer

*Acting Commissioner of Patents and Trademarks*